(12) United States Patent
Wrenn

(10) Patent No.: US 8,486,377 B1
(45) Date of Patent: *Jul. 16, 2013

(54) BEESWAX AND JOJOBA WAX EMULSION

(76) Inventor: Michael Joseph Wrenn, Hemet, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/546,362

(22) Filed: Jul. 11, 2012

(51) Int. Cl.
*A61K 8/97* (2006.01)
*A61K 35/64* (2006.01)
*A61K 36/00* (2006.01)
*A61K 36/33* (2006.01)
*A61K 9/14* (2006.01)
*A61K 8/98* (2006.01)

(52) U.S. Cl.
CPC ............ *A61K 35/64* (2013.01); *A61K 35/642* (2013.01); *A61K 35/644* (2013.01); *A61K 36/00* (2013.01); *A61K 36/33* (2013.01); *A61K 9/14* (2013.01); *A61K 8/97* (2013.01); *A61K 8/98* (2013.01); *Y10S 514/944* (2013.01)
USPC ............ 424/58; 424/725; 514/944; 516/98

(58) Field of Classification Search
None
See application file for complete search history.

(56) References Cited

U.S. PATENT DOCUMENTS

| 5,891,440 | A * | 4/1999 | Lansky | 424/727 |
| 8,241,612 | B2 * | 8/2012 | Wrenn | 424/58 |
| 2004/0235691 | A1 * | 11/2004 | Pham et al. | 510/130 |

OTHER PUBLICATIONS

Natural Facial Recipes (http://naturalfacialrecipes.homestead.com/eyeserumrecipes.html), dated May 30, 2009 (as of internet archive), 5 pages total (4 pages from web and 1 page from internet archive).*
A Dusick. "How to Make Beeswax Wood Polish." http://www.amberdusick.com/woodmouse_loves_crafts/2010/07/how-to-make-beeswax-wood-polish-woodmouse-recipe.html, Jul. 19, 2010, 15 printed pages.*
GF Spencer, RD Plattner, T Miwa. "Jojoba Oil Analysis by High Pressure Liquid Chromatography and Gas Chromatography/Mass Spectrometry." Journal of the American Oil Chemist's Society, vol. 54 No. 4, 1977, pp. 187-189.*

* cited by examiner

*Primary Examiner* — Frederick Krass
*Assistant Examiner* — Isaac Shomer
(74) *Attorney, Agent, or Firm* — James A. Italia; Italia IP

(57) ABSTRACT

A composition of matter and a method are disclosed including mixing pieces of solid beeswax and liquid jojoba wax at a predetermined temperature within a predetermined range of temperatures, filtering the mixture, and cooling the mixture to form a colloidal gel.

12 Claims, 2 Drawing Sheets

BEESWAX AND JOJOBA WAX EMULSION

CROSS-REFERENCE TO RELATED APPLICATION

This application is a Continuation Application of, and claims the benefit of priority to, U.S. non-provisional application Ser. No. 12/941,313, filed Nov. 08, 2010, now U.S. Pat. No. 8,241,612, the contents of which are incorporated herein by reference.

BACKGROUND OF INVENTION

This application relates generally to manufacturing and use of emulsions. More specifically, this application relates to manufacturing and use of beeswax and jojoba wax.

SUMMARY

In aspects of the present disclosures, a colloidal gel or partial gel is disclosed including beeswax and jojoba wax. The beeswax nanoparticles are suspended as disperse phase material in jojoba wax as dispersion phase material.

In further aspects of the present disclosures, a method of making a colloidal gel is disclosed including taking a particular quantity of beeswax by weight, and taking a particular quantity of jojoba wax by weight, such that the particular quantity of the jojoba wax is greater than, equal to or less than the particular quantity of the beeswax. The method further includes mixing the beeswax with the jojoba wax, and blending beeswax and the jojoba wax while maintaining a blending temperature in a predetermined range of temperatures to produce the colloidal gel In still further aspects of the disclosure, a method of delivering beeswax is disclosed including using a colloidal gel including beeswax and jojoba wax, wherein a weight proportion of the jojoba wax is greater than, equal to or less than a weight proportion of the beeswax in the colloidal gel, and wherein the beeswax is dispersed in the jojoba wax. The method further includes applying the colloidal gel to a surface of a target object to enable deep delivery or surface coating of the beeswax and jojoba wax to the surface of the target object by flow properties of the jojoba wax.

BRIEF DESCRIPTION OF THE DRAWINGS

The drawings, when considered in connection with the following description, are presented for the purpose of facilitating an understanding of the subject matter sought to be protected.

DETAILED DESCRIPTION

Figure 1:
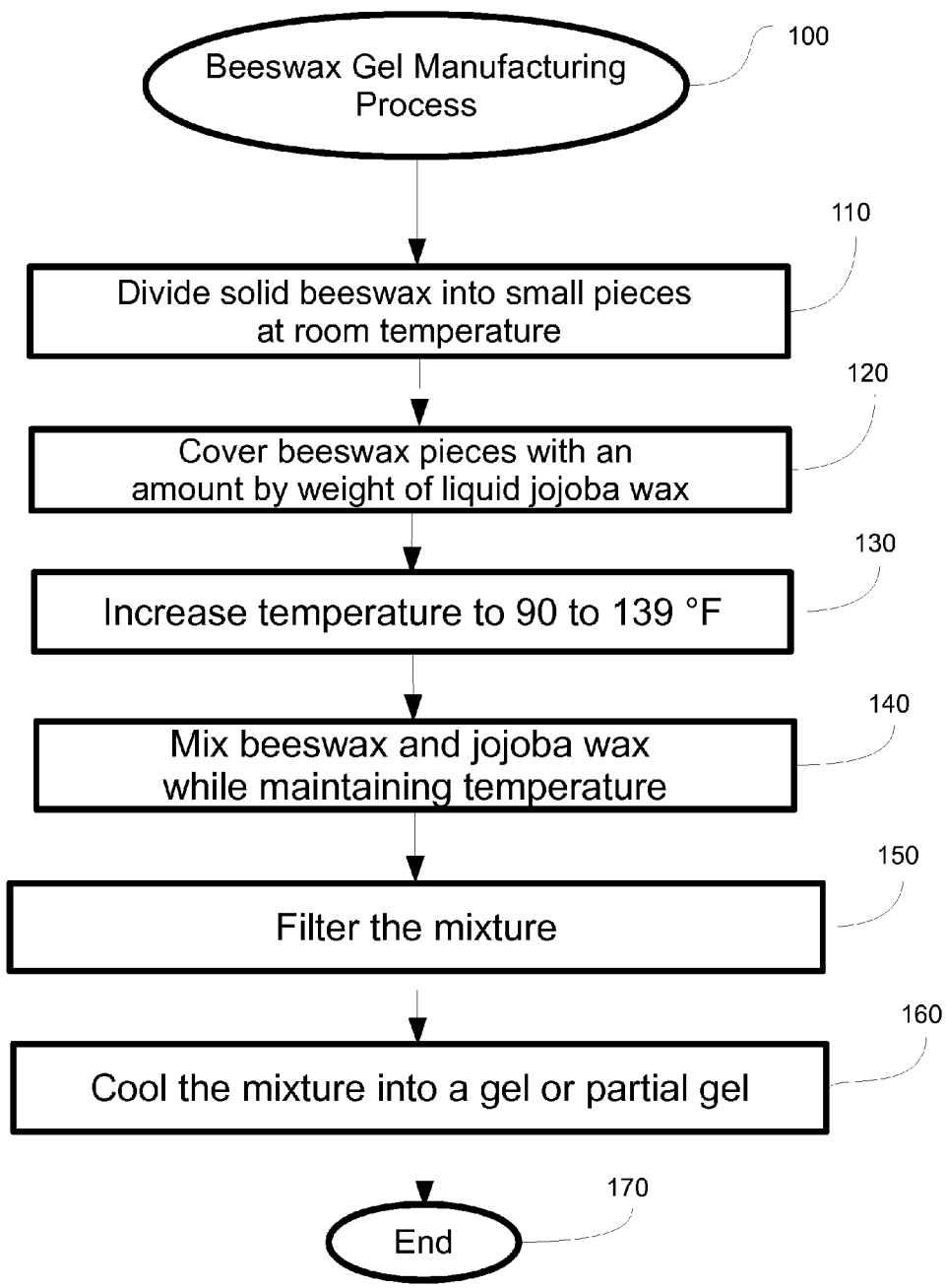
FIG. 1 shows a flow diagram of a process of making beeswax gel.

While the present disclosure is described with reference to several illustrative embodiments described herein, it should be clear that the present disclosure should not be limited to such embodiments. Therefore, the description of the embodiments provided herein is illustrative of the present disclosure and should not limit the scope of the disclosure as claimed. In addition, while following description references beeswax gel, it will be appreciated that the disclosure may be used with other types of mixtures of beeswax, such as emulsions, colloids, and the like.

Briefly described, a composition of matter and a method are disclosed including mixing pieces of solid beeswax and jojoba wax at a predetermined temperature within a predetermined range of temperatures, filtering the mixture, and cooling the mixture to form a gel or partial gel mixture.

An emulsion is a mixture of several immiscible (unblendable) liquids. Emulsions are types of colloids, a general class of two-phase compositions of matter. The two phases include a dispersed phase and a continuous phase, which is usually a liquid. Although the terms colloid and emulsion may be used interchangeably in some literature, emulsion tends to have both the dispersed and the continuous phase as liquid. In an emulsion, one substance (the disperse phase) is dispersed in the other (the continuous phase).

An emulsifier is a substance constituted from molecules having a hydrophilic head and a hydrophobic (oil-loving) tail. The hydrophilic head chemically bonds or attaches to the aqueous phase and the hydrophobic tail attaches to the oil phase. The emulsifier positions itself at the oil-water or air-water interface and, by reducing the surface tension, has a stabilizing effect on the emulsion, retarding or preventing the separation of mixture components.

Gel is a colloid in which the disperse phase has combined with the continuous (or dispersion) phase to produce a semi-solid material, such as a jelly.

The existing mixtures containing beeswax and jojoba wax are commonly used as emollients, enhancers, preservers, or restorers for skin, leather, wood, and other similar surfaces. The existing mixtures combine a number substances other than beeswax and jojoba wax, thus reducing or nullifying some of the properties and benefits of beeswax and jojoba wax, such as antibacterial properties, lubricity properties, ultra violet (UV) light blocking properties, and the like, as further detailed below. Such existing mixtures generally provide less than the full effect of all the benefits of a beeswax and jojoba wax combination in their natural form. A mixture, which is easy to apply and allows the substantially full benefits of beeswax and jojoba wax to be delivered to surfaces and materials to which beeswax and jojoba wax are applied is desirable.

In various embodiments, a colloidal gel comprising only solid beeswax and liquid jojoba wax, without any other substances in the mixture, is disclosed. Such a gel is substantially pure, constituting a naturally forming gel of two natural waxes, each of which have beneficial properties, which are substantially fully preserved and available in the gel. In these embodiments, the beeswax and jojoba wax are the sole ingredients. By combining beeswax and jojoba wax in certain ratios and at certain temperatures less than the melting point of beeswax, the colloidal gel is formed that is easy to use and may be applied at room temperatures for a multitude of purposes, as further detailed below. In various other embodiments, for some specific uses, scents such as essential oils may be added to the mixture. The beeswax used in the mixture may be pure, impure, and possibly chemically extracted.

In various embodiments, the colloidal beeswax gel allows the delivery of the benefits of natural beeswax at room temperature without melting the beeswax. Generally, beeswax is solid at room temperature, substantially precluding the effective application of beeswax into the body of material, such as skin, leather, wood, and the like when applied to the surface of the material. Accordingly, a chemical carrier, such as a dispersion medium is needed to carry beeswax particles deep into the body of the material, beyond its surface area, to which the beeswax is being applied. This may be accomplished by dispersing the beeswax molecules in liquid jojoba wax.

Due to the properties of each wax, when the beeswax and jojoba wax are combined with each other at temperatures less than the melting point of beeswax, which is about 140 degrees Fahrenheit (° F.) or 60 degrees Celsius (° C.), the combination may form a gel under certain blending conditions described below, that is easy to apply at room temperature and becomes softer at the normal metabolic temperature of the human body (98.6° F.). Since the properties of each of the two waxes are preserved in the gel, that is, the two waxes do not chemically combine, the benefits of each wax are preserved and are available to any material to which the gel is applied.

In various embodiments, when the jojoba wax and beeswax are mixed, the jojoba wax substantially acts as a carrier for the beeswax, allowing the beeswax to be more easily absorbed by the object surface and/or material to which the gel is being applied. After some period of time, the beeswax will stay absorbed in the body of the material, while the jojoba wax will separate from the beeswax and rise to the surface of the object it was applied to.

The process of making the gel or partial gel includes preparing the beeswax by dividing it into small pieces or strings, mixing appropriate proportions of beeswax and jojoba wax, manually or mechanically blending the two waxes at an appropriate temperature, filtering the mixture of the waxes, and allowing the mixture to cool into a gel. The resulting gel provides the beneficial properties associated with beeswax and jojoba wax individually. Some of these properties include but are not limited to cosmetic use, anti-bacterial use, lubrication for machinery and other mechanical parts, restoration and preservation of plastics, rubber, and leather, UV blocking, rust protection, and protective coating on hard and soft materials.

This composition is beneficial as an emollient and mammalian skin sun block, as a salve or as a poultice containing natural vitamin E to enhance the healing of wounds, scalp and follicle conditioning, as an enhancer, preserver, and restorer of many materials such as all forms of leather, wood, plastics, and as a non-petroleum lubricant and a rust inhibitor on all commonly used metals. The beeswax gel or partial gel may also be used as a lubricant for pipe jacking (a technique for installing underground pipelines, ducts and culverts, where powerful hydraulic jacks are used to push specially designed pipes through the ground behind a shield at the same time as excavation is taking place within the shield,) as petroleum lubricants are environmentally not desirable and their use may be prohibited in some areas.

Additionally, a cloth or other similar applicator used for applying the beeswax gel to a surface, when penetrated by the gel, does not become stiff and dry and remains supple and flexible for reuse at a later time.

In various embodiments, the above-mentioned properties are provided at least in part because of the natural combination of beeswax and jojoba wax without additives, and the process in which the composition is produced.

In various embodiments, in gel form, the beneficial properties of the beeswax and jojoba wax are combined. Beeswax retains its anti-fungal and anti-bacterial properties, and it also retains its ability to block ultra-violet rays. Beeswax also retains its adherence and lubricity. The jojoba wax retains its emollient properties, penetrating properties, lubricity properties, and dispersion properties to carry the gel into many of the materials on which it is applied. If the gel is made at temperatures below 139° F., the several forms of vitamin E naturally present in the Jojoba wax are also preserved. Thus the benefits of the vitamins E in the jojoba wax can be made available to mammalian skin at the organism's metabolic temperature. The beeswax properties of adherence holds the gel in place extending the time the benefits of the gel can be imparted upon the object and/or body part to which the gel is applied. When the gel is applied to materials and both the gel and the materials are at temperatures between 90° F. to 139° F., the gel begins liquefying (it liquefies completely at 128° F.) and may penetrate into the materials where it remains after they cool.

The beeswax gel may be used substantially wherever petroleum based or other types of lubricants may be used, but not under special conditions and purposes, such as elevated temperatures or as a substitute for engine oil. For example, the beeswax gel may be used to lubricate pipes, made of various materials, being jacked through earthen embankment.

The beeswax gel may be used for many applications, such as those mentioned previously. The beeswax gel may be used on mammal skin as cosmetic emollient, cosmetic nail conditioner; moisturizer; sun block; horse hoof conditioner, moisturizer, restorer; unguent for reducing age spots, unguent for maintaining or restoring healthy skin, unguent for nourishing and conditioning the scalp and hair follicles and conditioning the hair on the head; unguent for maintaining, restoring, healthy feet, reducing foot odor; unguent to aid in healing flesh and skin wounds; an unguent to aid in reducing scarring of the skin surface; topically applied plaque reducer for human and other mammalian teeth. Other uses of the beeswax gel so constituted include preserving, restoring, and conditioning leather; preventing or eliminating shoe odor by application of the gel on the interior of the shoe; preserving, restoring, and conditioning high-strength plastics; preserving, restoring, and conditioning rubber; preserving, restoring, and conditioning wood of all species; and providing a protective coating on most hard and soft surfaced materials including all the metals used in common fabrications.

FIG. 1 shows a flow diagram of a process of making beeswax gel. Process 100 proceeds to block 110, where the beeswax is divided into small pieces or strings at room temperature by grinding, grating, shredding, chopping, slicing, paring, and the like. These operations may be performed manually or by machines. Dividing the beeswax into smaller pieces increases the surface area of the solid beeswax for combining more readily with the liquid jojoba wax. The process proceeds to block 120.

At block 120, the beeswax is covered with liquid jojoba wax at a mixing temperature that is substantially equal to room temperature. In various embodiments, the proportion, by weight, of jojoba wax is generally several times the proportion of beeswax in the mixture. For example, a ratio of substantially 3 parts by weight of jojoba wax and substantially 1 part by weight of beeswax (ratio of 3j: 1b) may be used in a mixture. Other ratios may also be used, such as, a ratio of substantially 2j: 1b. Typically, the higher the ratio is in jojoba wax, the more fluid the composition will be, whereas, the lower the ratio is in jojoba wax, the more brittle the composition will be. The range of ratios of jojoba wax and beeswax in a mixture, which can effectively form a gel or partial gel is substantially 15j: 1b to 1j: 1b. A ratio of the amounts of the two waxes, by weight, which may have wide applicability is between substantially 2.5 to 5.0 parts jojoba wax to substantially 1 part beeswax. The process proceeds to block 130.

At block 130, the temperature of the mixture of the beeswax and jojoba wax is increased to a blending temperature in the blending range of 90° F. to 139° F. In various embodiments, the beeswax and the jojoba wax are heated to the blending temperature or other temperature in the blending range before mixing, and then they are mixed and blended. This change in temperature is affected by adding heat, which provides the energy needed for the jojoba wax to break down a crystal structure of the beeswax and allow the jojoba wax liquid to intermingle with beeswax nanoparticles to form a colloidal dispersion. In this mixture, the beeswax particles constitute the suspended particles or disperse phase and the jojoba liquid constitutes the dispersion phase or continuous phase. At ratios between 2.0 to 4.0 parts, by weight, jojoba wax to 1 part beeswax and at temperatures between 90° F. and 139° F., the properties of the two waxes interact by first breaking down the crystalline structure of the beeswax into nanoparticles, which form a network of nanostructures spanning the volume of jojoba wax liquid medium and result in a gel. The process proceeds to block 140.

At block 140, the beeswax and the jojoba wax are thoroughly mixed while maintaining the blending temperature in the range of 90° F. to 139° F. The waxes are blended together using hand mixing and pressing or by using a mechanical mixer such as a vertical propeller mixer. The Mixing of the components in the mixture may be done partially or entirely by vertical propeller mixers, centrifuges, roller presses, stamping presses, and other mechanical processes. Computers may be used to control various partially or fully automated processes to make and package this gel. The two waxes are blended as completely as practical and sufficiently to form a colloidal dispersion. The process proceeds to block 150.

At block 150, the mixture is filtered, for example, using a sieve, removing any particles of beeswax that are not part of the colloidal dispersion. Sieving the mixture creates a more smooth and pure gel. The process proceeds to block 160.

At block 160, the heated mixture is cooled. In various embodiments, the mixture is allowed to cool naturally, while in other embodiments, the mixture is actively cooled using air flow, refrigeration, and other similar methods of cooling. The process proceeds to block 170.

At block 170, the process terminates.

Figure 2:
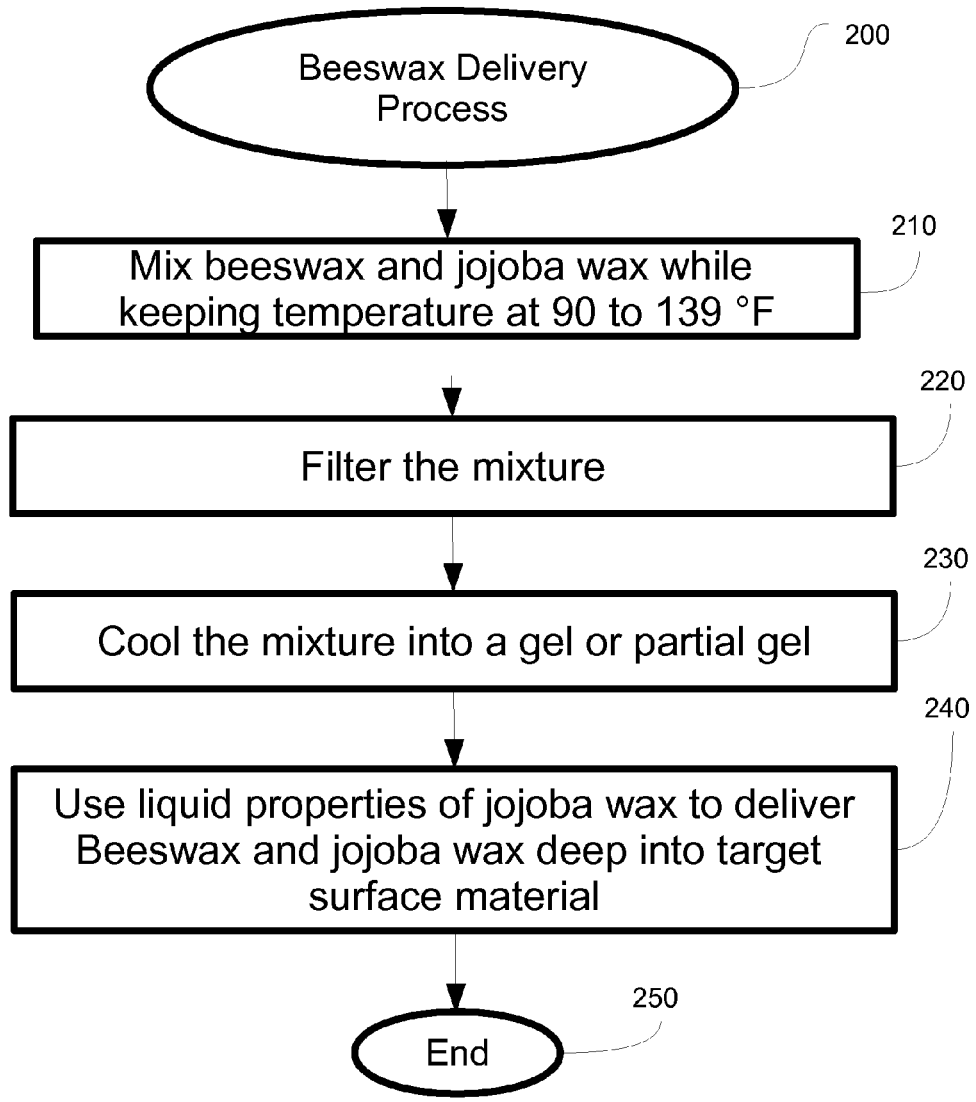
FIG. 2 shows an example flow diagram of a process of delivering beeswax using jojoba wax properties.

FIG. 2 shows an example flow diagram of a process of delivering beeswax using jojoba wax properties. Process 200 proceeds to block 210, where beeswax and jojoba wax are mixed while maintaining a temperature between 90° F. and 139° F. to produce a gel, as described in detail above with respect to FIG. 1. The process proceeds to block 220.

At block 220, the gel is filtered, for example, using a sieve, to separate any beeswax particles not dispersed in the colloidal gel. The process proceeds to block 230.

At block 230, the gel or partial gel is allowed to cool to room temperature. The process proceeds to block 240.

At block 240, the gel is applied to the surface of a target object, for example, by rubbing the gel on the target object by hand or with a cloth, sponge, or other similar applicator, to deliver the suspended particles of beeswax deep into the surface and subsurface material of the target object. The target object may include human skin, teeth, nails, horse hooves, leather, metals, mechanical parts, and others as described above. The fluid properties of jojoba wax enables the delivery of beeswax nanoparticles suspended therein as disperse phase material, by flowing such beeswax nanoparticles at microscopic levels into pores, crevices, and other porous inlets of surfaces and materials of the target object. After some time, the liquid jojoba wax may float to the surface of the material to which the gel was applied, leaving beeswax particles deep inside the material to continue providing the beeswax's properties to the material to which the gel was applied. The beeswax properties include antibacterial properties, sun UV protection, rust protection, and the like, as described previously. The process proceeds to block 250.

At block 250, the process terminates.

Changes can be made to the claimed invention in light of the above Detailed Description. While the above description details certain embodiments of the invention and describes the best mode contemplated, no matter how detailed the above appears in text, the claimed invention can be practiced in many ways. Details of the system may vary considerably in its implementation details, while still being encompassed by the claimed invention disclosed herein.

Particular terminology used when describing certain features or aspects of the disclosure should not be taken to imply that the terminology is being redefined herein to be restricted to any specific characteristics, features, or aspects of the disclosure with which that terminology is associated. In general, the terms used in the following claims should not be construed to limit the claimed invention to the specific embodiments disclosed in the specification, unless the above Detailed Description section explicitly defines such terms. Accordingly, the actual scope of the claimed invention encompasses not only the disclosed embodiments, but also all equivalent ways of practicing or implementing the claimed invention.

The above specification, examples, and data provide a complete description of the manufacture and use of the claimed invention. Since many embodiments of the claimed invention can be made without departing from the spirit and scope of the disclosure, the invention resides in the claims hereinafter appended. It is further understood that this disclosure is not limited to the disclosed embodiments, but is intended to cover various arrangements included within the spirit and scope of the broadest interpretation so as to encompass all such modifications and equivalent arrangements.

What is claimed is:

1. A colloidal gel comprising:
   beeswax;
   jojoba wax, wherein beeswax nanoparticles are suspended as disperse phase material in jojoba wax as dispersion phase material; and
   wherein the colloidal gel consists of only the beeswax and the jojoba wax.

2. The colloidal gel of claim 1, wherein the ratio of the beeswax and the jojoba wax is in the range of 15 parts by weight of jojoba wax and 1 part by weight of beeswax to 1 part by weight of jojoba wax and 1 part by weight of beeswax.

3. The colloidal gel of claim 2, wherein the ratio of the beeswax and the jojoba wax is substantially 3 parts by weight of jojoba wax and substantially 1 part by weight of beeswax.

4. A method of making a colloidal gel, the method comprising:
   taking a particular quantity of beeswax by weight;
   taking a particular quantity of jojoba wax by weight, wherein the particular quantity of the jojoba wax is greater than the particular quantity of the beeswax;
   mixing the particular quantity of beeswax with the particular quantity of jojoba wax;
   blending the particular quantity of beeswax and the particular quantity of jojoba wax while maintaining a blending temperature in a predetermined range of temperatures to produce the colloidal gel; and
   dividing the beeswax into smaller pieces.

5. The method of claim 4, further comprising mixing the particular quantity of beeswax and the particular quantity of jojoba wax at a mixing temperature substantially equal to room temperature.

6. The method of claim 5, further comprising increasing the mixing temperature to the blending temperature.

7. The method of claim 4, further comprising filtering the colloidal gel to eliminate beeswax particles not dispersed in the colloidal gel.

8. The method of claim 4, further comprising cooling the colloidal gel.

9. The method of claim 4, wherein the particular quantity of jojoba wax is three times greater than the particular quantity of beeswax.

10. The method of claim 4, wherein the predetermined range of temperatures is 90° F. to 139° F.

11. A method of delivering beeswax, the method comprising:
   using a colloidal gel including beeswax and jojoba wax, wherein a weight proportion of the jojoba wax is greater than a weight proportion of the beeswax in the colloidal gel, and wherein the beeswax is dispersed in the jojoba wax;
   applying the colloidal gel to a surface of a target object to enable deep delivery of the beeswax to the surface of the target object by flow properties of the jojoba wax; and
   wherein beeswax and jojoba wax are substantially the only ingredients in the colloidal gel.

12. The method of claim 11, wherein the weight proportion of jojoba wax is at least two times greater than the weight proportion of the beeswax in the colloidal gel.

\* \* \* \* \*